US00PP32222P3

(12) United States Plant Patent
Martinelli et al.

(10) Patent No.: US PP32,222 P3
(45) Date of Patent: Sep. 22, 2020

(54) STRAWBERRY PLANT NAMED 'CIVRH621'

(50) Latin Name: ***Fragaria* x *ananassa***
Varietal Denomination: CIVRH621

(71) Applicant: C.I.V.—CONSORZIO ITALIANO VIVAISTI—SOCIETÀ CONSORTILE A R.L., Comacchio FE (IT)

(72) Inventors: Alessio Martinelli, Ferrara (IT); Michelangelo Leis, Ferrara (IT)

(73) Assignee: C.I.V.—CONSORZIO ITALIANO VIVAISTI—SOCIETA CONSORTILE A R.L., Comacchio (IT)

( * ) Notice: Subject to any disclaimer, the term of this patent is extended or adjusted under 35 U.S.C. 154(b) by 0 days.

(21) Appl. No.: 16/602,448

(22) Filed: Oct. 8, 2019

(65) Prior Publication Data

US 2020/0120844 P1 Apr. 16, 2020

(30) Foreign Application Priority Data

Oct. 10, 2018 (QZ) ..... PBR 2018/2555

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 5/08; A01H 6/74
See application file for complete search history.

*Primary Examiner* — Annette H Para
(74) *Attorney, Agent, or Firm* — Foley & Lardner LLP

(57) ABSTRACT

This invention relates to a new and distinct variety of strawberry plant named 'CIVRH621'. This new everbearer strawberry plant named 'CIVRH621' is primarily adapted to the climate and growing conditions of the high chill areas. It is characterized as a rustic plant resistant to mildew with a robust and efficient root system tolerant to diseases, suitable for organic cultivation. 'CIVRH621' has high production during the initial harvesting period but is also long and constant through the season. The plant has high-medium vigor with semi-upright habit and medium density foliage. The fruit has a conical/hearted shape, which is maintained during the whole picking season, very attractive and uniform bright red color, also excellent skin resistance during the summer with good shelf life. The aroma of the fruit is intense and persistent with very pleasant organoleptic characteristics and an ideal balance between sweetness and acidity. Fruit picking is easy and fast.

4 Drawing Sheets

Figure 1:
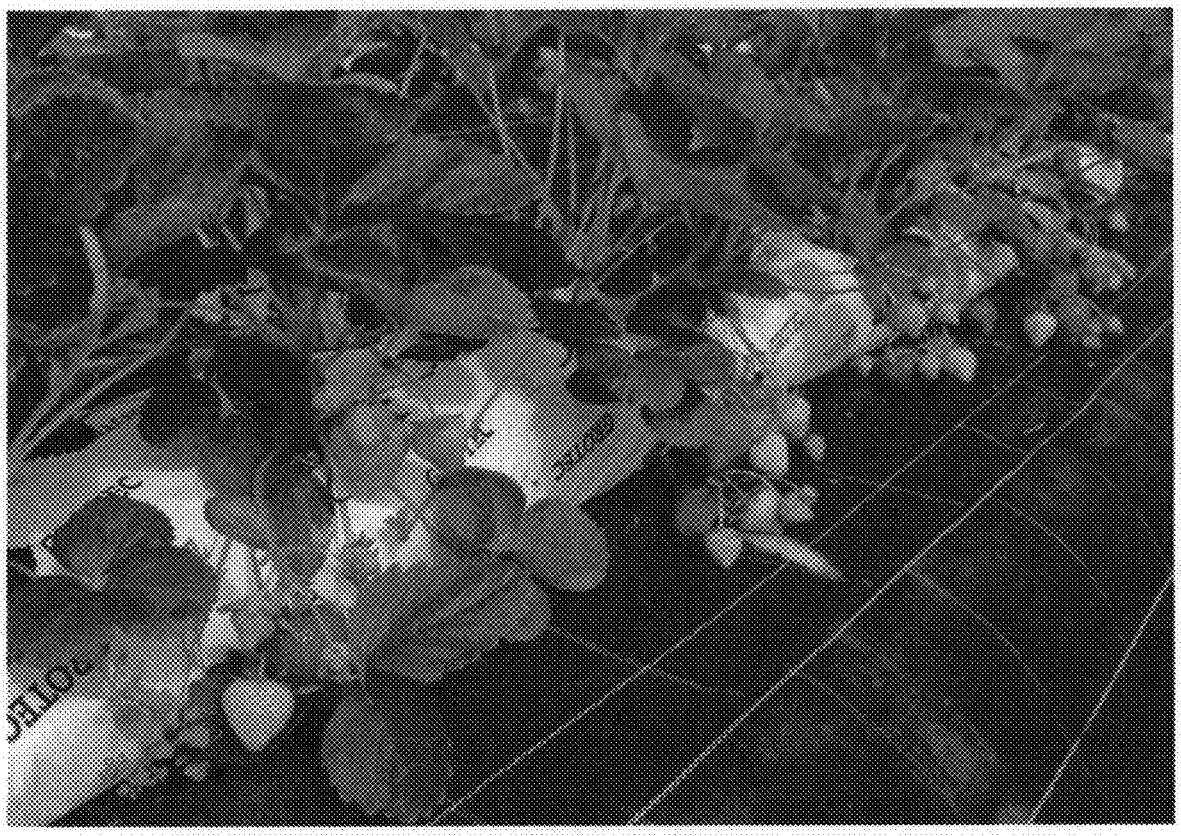

Latin name of the genus and species of the plant claimed: *Fragaria* x *ananassa.*

Variety denomination: 'CIVRH621'.

BACKGROUND OF THE INVENTION

The present invention relates to a new and distinct strawberry variety named 'CIVRH621'.

The new strawberry 'CIVRH621' is a product of a planned breeding program conducted by the inventor(s), Leis Michelangelo and Martinelli Alessio, in San Giuseppe di Comacchio (Ferrara), Italy. The objective of the breeding program is to develop new everbearer strawberry varieties with high chill requirement, rustic plants with robust and efficient root systems and good tolerance to diseases. Plants show resistance to mildew and are suitable for organic cultivation. Select fruits with very pleasant organoleptic characteristic and ideal balance between sweetness and acidity.

This new strawberry 'CIVRH621' is a result of a controlled cross made by the inventors in 2011, in San Giuseppe di Comacchio (Ferrara), Italy. The female or seed parent is the not released selection of Consorzio Italiano Vivaisti named 3H1F-11. The male or pollen parent is the not released selection of Consorzio Italiano Vivaisti named S7V9-9.

The new strawberry 'CIVRH621' was discovered and selected by the inventors as a single flowering plant within the progeny of the stated cross in 2013 in San Giuseppe di Comacchio (Ferrara), Italy. After its selection, the new variety was asexually propagated by stolons in a nursery located in San Giuseppe di Comacchio (Ferrara), Italy. The new variety was tested over the next several years at Consorzio Italiano Vivaisti in San Giuseppe di Comacchio (Ferrara), Italy and in different European areas with high chill conditions. This propagation has demonstrated that the combination of characteristics as herein disclosed for the new cultivar are firmly fixed and retained through successive generations of asexual reproduction. The new cultivar reproduces true to type.

BRIEF SUMMARY OF THE INVENTION

'CIVRH621' is an everbearer variety with high chill requirement.

The following traits have been repeatedly observed and are determined to be unique characteristics of 'CIVRH621', which in combination distinguish this strawberry plant as a new and distinct variety:

1. everbearer variety with high chill requirement;
2. rustic plant resistance to mildew with good tolerance to root system disease;

3. robust and efficient root system;
4. very high productivity, long and constant through the season;
5. bright red color, attractive and uniform; and
6. easy and fast fruit picking.

Of the many commercial cultivars known to the present inventor, the most similar in comparison to the new strawberry variety 'CIVRH621' is the patented strawberry variety Murano. Plants of the new strawberry variety 'CIVRH621' differ from plants of strawberry variety 'Murano' in the characteristics described in Table 2:

TABLE 2

| Characteristic | 'CIVRH621' | 'MURANO' |
|---|---|---|
| Fruit: attitude of sepal | Downwards | Outwards |
| Terminal leaflet: shape in cross | Straight | Concave |
| Plant: vigor | Strong | Medium to strong |

BRIEF DESCRIPTIONS OF THE PHOTOGRAPHS

The accompanying color photographs illustrate the overall appearance of typical specimens of the new strawberry variety 'CIVRH621', at various stages of development as true as it is reasonably possible with color reproductions of this type. Color in the photographs may differ slightly from the color value cited in the botanical description which accurately describe the color of 'CIVRH621'.

The depicted plant and plant parts of the new strawberry variety 'CIVRH621' were taken in San Giuseppe di Comacchio (Ferrara), Italy, and are approximately 3 to 5 months old.

Figure 2:
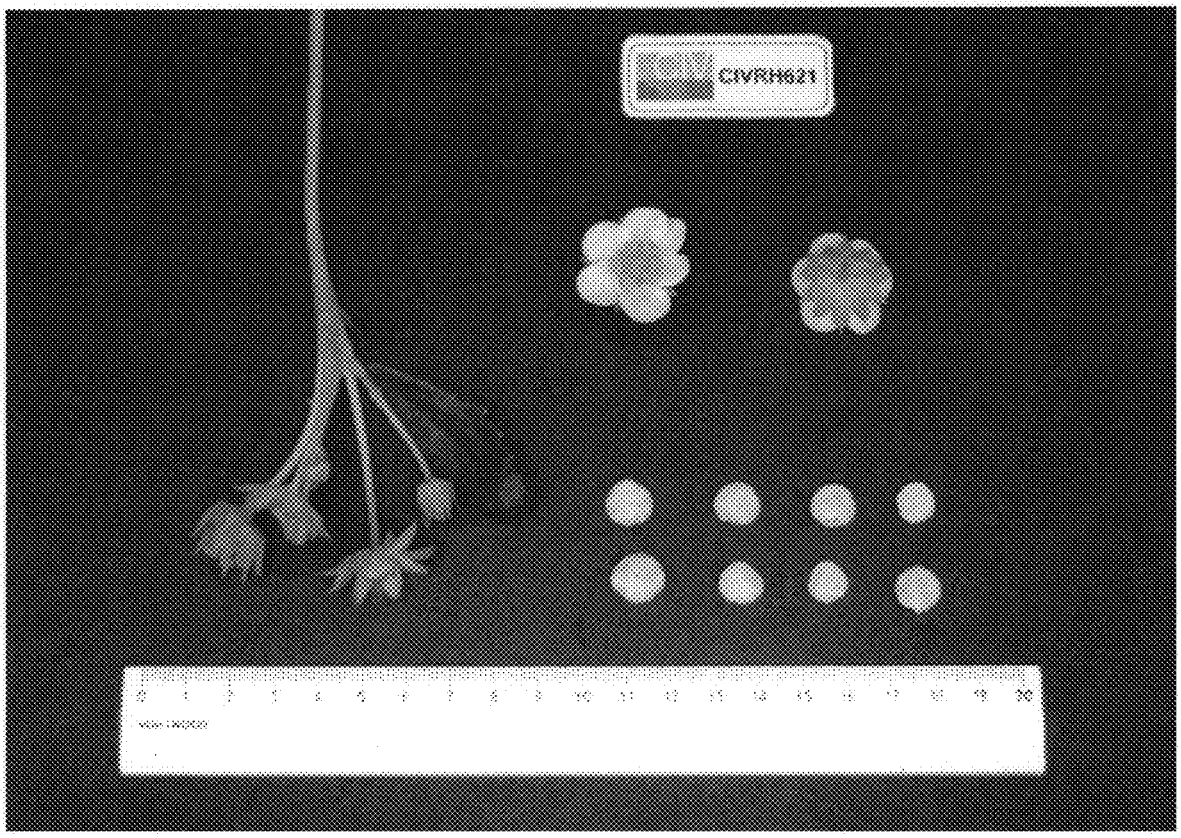
Figure 3:
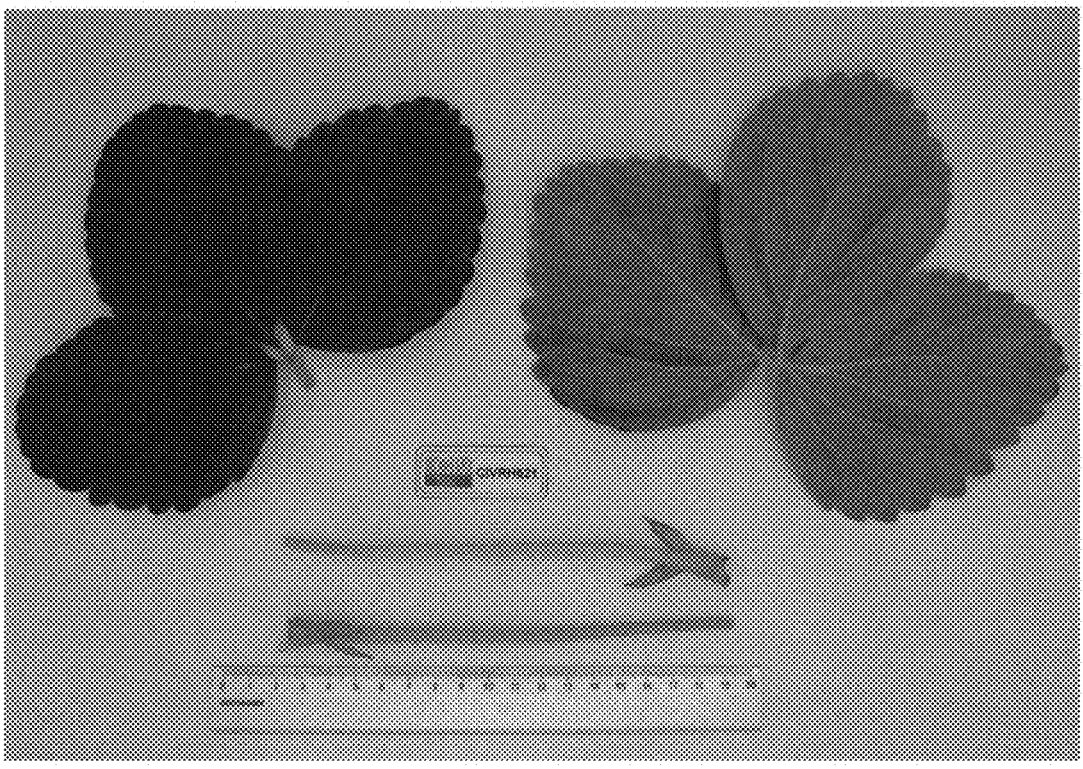
Figure 4:
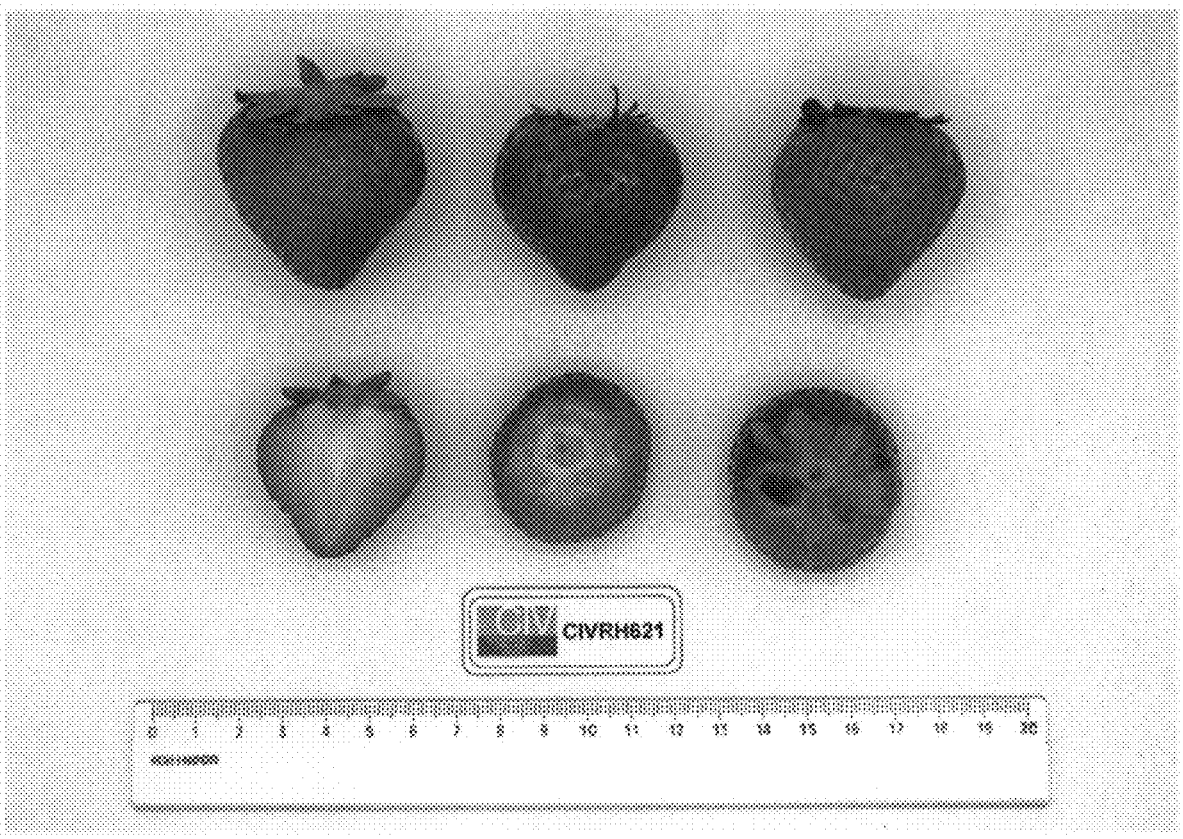

FIG. 1 shows typical plant of 'CIVRH621';
FIG. 2 shows typical flowers of 'CIVRH621';
FIG. 3 shows typical leaves of 'CIVRH621';
FIG. 4 shows typical fruits of 'CIVRH621'.

DETAILED BOTANICAL DESCRIPTION

'CIVRH621' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'CIVRH621', unless otherwise noted, taken during the 2018 growing season in San Giuseppe di Comacchio (Ferrara), Italy. The observations, measurements and values were taken from plants of 'CIVRH621' dug from a low-elevation nursery located in San Giuseppe di Comacchio (Ferrara), Italy, during 2018 and planted approximately 4 months later in San Giuseppe di Comacchio (Ferrara), Italy. Plants of the new strawberry variety 'CIVRH621' were grown under conditions which closely approximate those generally used in commercial practice.

Yield observations and fruit quality characteristics are averaged from 2 years of data collected from the 2017 through 2018 growing seasons. Flower measurements and characteristics are from secondary flowers unless otherwise noted. Fruit characteristics and measurements are from secondary fruit unless otherwise noted.

Color references are made to The Royal Horticultural Society Colour Chart (R.H.S.), 2001, except where general colors of ordinary significance are used. Color values were taken under daylight conditions at approximately 10:00 A.M. in San Giuseppe di Comacchio (Ferrara), Italy. The approximate age of the observed plants is 3 to 5 months.

The following tables 3-9 describe fruit, plant, stolon, foliage, fruiting truss, flower and pest/disease characteristics of the new strawberry 'CIVRH621'.

TABLE 3

FRUIT CHARACTERISTICS

| Characteristic | 'CIVRH621' |
|---|---|
| Color of mature fruit | Red (45A red group) |
| Color of internal flesh | Orange red (32A orange-red group) |
| Length (cm) | Average 4.1 cm |
| Width (cm) | Average 4.4 cm |
| Ratio length/width | 0.95 |
| Calyx diameter (cm) | Average 3.2 cm |
| Average weight (gm) | Average 21.8 gm in 2018 |
| Achene color | Yellow (1A green-yellow group) |
| Number of achenes per $cm^2$ | Average 9.5 achenes/$cm^2$ |
| Marketable yield (gm/pit) | Average 900-1100 gm/plt |
| Size | Large |
| Predominant shape | Conical |
| Difference in shape between primary and secondary fruit | None or very slight |
| Band without achenes | Absent |
| Unevenness of surface | Even or very slightly uneven |
| Evenness of color | Even or very slightly uneven |
| Glossiness | Strong |
| Insertion of achenes | Level with the surface |
| Insertion of calyx | Level with the surface |
| Attitude of the calyx | Outward |
| Size of calyx in relation to fruit diameter | Slightly smaller |
| Adherence of calyx | Very strong |
| Firmness of skin | Firm |
| Firmness of flesh | Firm |
| Distribution of red color of the flesh | Marginal |
| Hollow center expression | Absent or small |
| Flavor | Very good flavor with a balanced sugar-acid ratio |
| Soluble solids (% brix) | 8.6° Brix |
| Time of first flowering | Early |
| Time of first harvesting | Early (first picking the $30^{th}$ of May 2019 in San Giuseppe di Comacchio, Ferrara, Italy) |
| Harvest period | From the end of May to October |
| Type of bearing | Day neutral |

TABLE 4

PLANT CHARACTERISTICS

| Characteristic | 'CIVRH621' |
|---|---|
| Height (cm) | Average 30 cm |
| Spread (cm) | Average 38 cm |
| Size | Medium |
| Habit | Upright |
| Density | Dense |
| Vigor | Medium |

TABLE 5

| STOLON CHARACTERISTICS | |
|---|---|
| Characteristic | 'CIVRH621' |
| Average number per plant | About 15 stolons/mother plant in our nursery in San Giuseppe di Comacchio (Ferrara) Italy |
| Anthocyanin coloration | Purple (184A greyed-purple group) |
| Anthocyanin intensity | Weak to medium. The anthocyanin coloration is present in the apical part of the stolon. |
| Diameter at bract (mm) | Average 4.1 mm |
| Pubescence | Medium |

TABLE 6

| FOLIAGE CHARACTERISTICS | |
|---|---|
| Characteristic | 'CIVRH621' |
| Foliage: | |
| Color of upper surface | Green (137A green group) |
| Color of underside | Green (137C green group) |
| Shape in cross section | Concave |
| Interveinal blistering | Medium |
| Glossiness | Medium |
| Number of leaflets | Three (3) |
| Terminal Leaflet: | |
| Length (cm) | Average 11.5 cm |
| Width (cm) | Average 9 cm |
| Length/width ratio | 1.2 |
| Serrations/leaf | Free to touching |
| Size | Medium |
| Shape of base | Acute |
| Shape of teeth | Serrate to crenate |
| Petiole: | |
| Length (cm) | Average 18.8 cm |
| Diameter (mm) | Average 4.8 mm |
| Petiolule length (mm) | Average 6.1 mm |
| Pubescence | Weak |
| Attitude of hairs | Upwards |
| Stipule: | |
| Length (mm) | Average 17.8 cm |
| Width (mm) | Average 8.9 mm |
| Anthocyanin coloration | Weak |
| Color | Red-purple (59C red-purple group) |

TABLE 7

| FRUITING TRUSS CHARACTERISTICS | |
|---|---|
| Characteristic | 'CIVRF1621' |
| Length (cm) | Average 28 cm |
| Position relative to foliage | Above the foliage |
| Pubescence | Strong |

TABLE 7-continued

| FRUITING TRUSS CHARACTERISTICS | |
|---|---|
| Characteristic | 'CIVRF1621' |
| Anthocyanin intensity | None to very light |
| Attitude at first pick | Outwards |

TABLE 8

| FLOWER CHARACTERISTICS | |
|---|---|
| Characteristic | 'CIVRH621' |
| Petal color | |
| Mature (upper) | White (155 D white group) |
| Mature (lower) | White (155 D white group) |
| Petal shape | |
| Overall | Rounded |
| Apex | Rounded |
| Base | Straight |
| Petal length (mm) | Average 12.6 mm |
| Petal width (mm) | Average 11.5 mm |
| Petal length/width ratio | 1.09 |
| Number of petals/flower | About 7 to 8 |
| Sepals color | |
| Mature (upper) | Green (141 B green group) |
| Mature (lower) | Green (144 A green group) |
| Sepal shape | |
| Overall | Narrow-elliptic |
| Apex | Pointed |
| Base | Narrow |
| Sepal length (mm) | Average 10.6 mm |
| Sepal width (mm) | Average 4.7 mm |
| Sepal length/width ratio | 2.6 |
| Number of sepals/flower | About 15 |
| Corolla diameter (mm) | Average 33.2 mm |
| Calyx diameter (mm) | Average 33.5 mm |
| Size of calyx relative to corolla | Same size |
| Relative position of petals | Touching to overlapping |

TABLE 9

| PEST AND DISEASE REACTIONS |
|---|
| The 'CIVRH621' variety has been tested for several years and it has demostrated good tolerance to diseases of the root system and resistance to mildew. |

We claim:

1. A new and distinct strawberry plant named 'CIVRH621', as herein described and illustrated by the characteristics set forth above.

* * * * *